United States Patent [19]

Comer et al.

[11] 3,993,776

[45] Nov. 23, 1976

[54] ANOREXIGENIC PROCESS AND COMPOSITION

[75] Inventors: William T. Comer; Herbert R. Roth, both of Evansville, Ind.

[73] Assignee: Mead Johnson & Company, Evansville, Ind.

[22] Filed: Oct. 21, 1975

[21] Appl. No.: 624,346

Related U.S. Application Data

[62] . Division of Ser. No. 406,524, Oct. 15, 1973, Pat. No. 3,919,424, which is a division of Ser. No. 229,202, Feb. 16, 1972, Pat. No. 3,801,631.

[52] U.S. Cl. .................................. 424/316; 424/321
[51] Int. Cl.$^2$ ....................................... A61K 31/205
[58] Field of Search ............................ 424/321, 316

[56] References Cited
UNITED STATES PATENTS 3,341,584　9/1967　Larsen et al. ....................... 424/330
3,634,511　1/1972　Howe et al. ......................... 424/324

OTHER PUBLICATIONS

Physician's Desk Reference, 25th Edition, (1971), pp. 756, 1492–1493.

Larsen et al., Nature, vol. 23, No. 4951, pp. 1283–1284, (9/19/64).

Uloth et al., J. Med. Chem. 9, pp. 88–97, (1966).

Larsen et al., J. Med. Chem. 10, pp. 462–472, (1967).

*Primary Examiner*—Norman A. Drezin
*Attorney, Agent, or Firm*—R. E. Carnahan; R. H. Uloth

[57] ABSTRACT

2'-Hydroxy-5'-[1-hydroxy-2-(2-methyl-1-phenyl-2-propylamino)ethyl]methanesulfonanilide is a potent anorexigenic agent and orally active bronchodilator.

4 Claims, No Drawings

ANOREXIGENIC PROCESS AND COMPOSITION

CROSS REFERENCE TO RELATED APPLICATIONS

This application is a division of our co-pending application Ser. No. 406,524 filed Oct. 15, 1973 and now U.S. Pat. No. 3,919,424 which in turn is a division of prior co-pending application Ser. No. 229,202 filed Feb. 16, 1972 and now U.S. Pat. No. 3,801,631 patented Apr. 2, 1974.

FIELD OF THE INVENTION

This invention is in the field of drug, bio-affecting, and body treating compositions containing an organic active ingredient and deals specifically with the sulfonic acid amide 2'-hydroxy-5'-[1-hydroxy-2-(2-methyl-1-phenyl-2-propylamino)ethyl]methanesulfonanilide. This substance is referred to for convenience as MJ 9184. Its structural formula is given below.

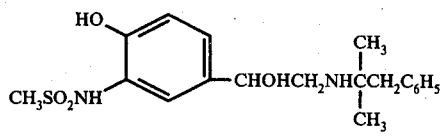

DESCRIPTION OF PRIOR ART

The following references relate to a broad genus of sulfonic acid amides of which the present substance is a newly synthesized member. It has a number of outstanding qualities as compared to its congeners.

1. Aubrey A. Larsen, et al., U.S. Pat. No. 3,341,584 patented Sept. 12, 1967.
2. A. A. Larsen, et al., *Nature*, Vol. 203, No. 4951, pp. 1283–1284, Sept. 19, 1964.
3. Robert H. Uloth, et al., *J. Med. Chem.*, 9, 88–97 (1966).
4. A. A. Larsen, et al., *J. Med. Chem.*, 10, 462–472 (1967).

Reference No. 4 deals specifically with the sulfonanilides most closely related structurally to MJ 9184. One substance from this series, 2'-hydroxy-5'-(1-hydroxy-2-isopropylaminoethyl)methanesulfonanilide (Compound No. 49 in the publication) was reported by the authors to be equivalent in potency to isoproterenol and to have been the subject of clinical evaluation as a bronchodilator. That substance has been referred to in the literature as MJ 1992 and as soterenol. Other members of the series are described by the authors as uterine relaxants, namely 2'-hydroxy-5'-[1-hydroxy-2-(4-methoxyphenethylamino)propyl]methanesulfonanilide and 2'-hydroxy-5'-[1-hydroxy-2-(1-phenoxy-2-propylamino)propyl]methanesulfonanilide. The same three substances are also referred to as vasodilators, smooth muscle relaxants, and as bronchodilators at Column 24 of the Larsen, et al. patent cited above as reference No. 1.

SUMMARY OF THE INVENTION

The compound of the present invention is prepared according to the generalized method outlined in foregoing references Nos. 1 and 4. 5'-Bromoacetyl-2'-hydroxymethanesulfonanilide is caused to react in a neutral organic solvent with α-α-dimethylphenethylamine and the resulting aminoacetylsulfonanilide is hydrogenated over a catalyst to provide the desired compound. Detailed procedures are given in our U.S. Pat. No. 3,801,631 for this method. The invention relates to the anorexigenic process using the compound and its salts, and to pharmaceutical compositions adapted for use in the process. MJ 9184 is an anorexigenic agent having a potency on a dosage weight basis 10 times that of amphetamine. It is thus an outstandingly active drug. It also possesses analgesic activity.

The method of Randall, et al., *J. Pharmacol. Exper. Therap.*, 129, 163–171 (1960) is suitable for demonstration of the anorexic action of MJ 9184. This test involves the comparison of the food consumption of groups of fasted rats during a 4 hr. feeding period normally, and after intraperitoneal injection of a selected dose of the test drug prior to feeding. Amphetamine sulfate, a widely used anorexic substance, at a dose of 2.2 mg./kg. reduces food consumption to ½ of normal. A 50% reduction of food consumption is achieved at a dose of 0.25 mg./kg. of MJ 9184 hydrochloride.

MJ 9184 hydrochloride is a relatively non-toxic substance, the $LD_{50}$ being in excess of 6000 mg./kg. for mice treated orally, greater than 4000 mg./kg. for rats treated orally, and 304 mg./kg. for mice treated intraperitoneally. Cats tolerate doses of 256 mg./kg. orally with only mild signs, but no lethality.

MJ 9184 and its pharmaceutically acceptable salts are administered to reduce the food intake of obese mammals at doses in the range of 2 mcg./kg. to 1 mg./kg. of body weight. The substances may be administered orally, parenterally, or by inhalation. The usual human dose is 2 to 20 mcg./kg. of body weight 1 to 4 times a day. Suitable dosage compositions are described below.

The present invention includes the pharmaceutically acceptable metal and acid addition salts of MJ 9184. Examples of metal salts include the sodium, potassium, calcium, magnesium, aluminum, and zinc salts. The sulfonanilide group is the acidic function which is neutralized in forming metal salts. Acid addition salts are formed at the amino group. Examples of pharmaceutically acceptable acid addition salts are the hydrochloride, hydrobromide, sulfate, phosphate, nitrate, mucate, isethionate, acetate, propionate, gluconate, benzoate, mesylate, tosylate, etc. Both types of salts can be prepared by reaction, preferably in solution of chemically equivalent amounts of MJ 9184 and the desired acid or base. They may be prepared by metathesis, preferably in a liquid reaction medium. A number of the acid addition salts including the hydrochloride salt have very low solubilities. The isethionate salt is notable for its water solubility and is particularly suited for parenteral formulations and for the preparation of solutions for nebulization. The term pharmaceutically acceptable used with reference to the salts implies a lack of toxicity in the doses required for the intended uses, and the possession of physical properties adapting the substances for one or more of the intended uses.

EXAMPLE A

Capsules

The following ingredients are blended in a twin shell blender and then loaded into No. 4 two-piece hard gelatin capsules. The batch size is sufficient for 1000 capsules and provides for a fill weight of 160 mg. supplying 0.5 mg. of active ingredient per capsule.

| | |
|---|---|
| 2'-Hydroxy-5'-[1-hydroxy-2-(2-methyl-1-phenyl-2-propylamino)ethyl]methanesulfonanilide hydrochloride | 0.5 g. |
| Lactose, impalpable | 159.5 g. |

By adjusting the ingredient weights, capsules containing from 0.2 mg. to 2.0 mg. of active ingredient may be prepared in the same fashion.

EXAMPLE B

Tablets

The following ingredients when thoroughly blended in the dry state in a twin shell blender provide a composition suitable for tableting in a standard tablet press using a ½ inch concave die. The batch size is sufficient for 1000 tablets containing 0.2 mg. of active ingredient per tablet.

| | |
|---|---|
| 2'-Hydroxy-5'-[1-hydroxy-2-(2-methyl-1-phenyl-2-propylamino)ethyl]methanesulfonanilide hydrochloride | 0.2 g. |
| Sucrose, Pregranulated for direct compression | 77.3 g. |
| Corn starch | 2.0 g. |
| Crystalline cellulose | 20.0 g. |
| Magnesium stearate | 0.5 g. |

EXAMPLE C

Solution for Nebulization

The following ingredients are used to prepare a solution which is clarified by filtration and then filled into 10 ml. amber glass bottles.

| | |
|---|---|
| 2'-Hydroxy-5'-[1-hydroxy-2-(2-methyl-1-phenyl-2-propylamino)ethyl]methanesulfonanilide isethionate | 13.33 g. |
| Sodium bisulfite | 2.00 g. |
| Chlorobutanol, USP | 5.00 g. |
| Propylene glycol | 50.00 g. |
| Sodium saccharin | 1.00 g. |
| Citric acid, anhydrous | 1.92 g. |
| Purified water | qs 1000 ml. |
| Sodium hydroxide | qs pH 3.75 |

The foregoing solution is suitable for administration in conventional nebulization equipment adapted for administration of drugs by inhalation. This solution contains 1,33% by weight of the isethionate salt equivalent to 1% by weight of MJ 9184 base. The concentration of active ingredients may be varied to provide similar solutions containing an amount of the isethionate salt equivalent to from 0.25 to 2% by weight of MJ 9184 base.

EXAMPLE D

Aerosol Dispenser

A solution of 2.0 g. of 2'-hydroxy-5'-[1-hydroxy-2-(2-methyl-1-phenyl-2-propylamino)ethyl]methanesulfonanilide isethionate in 373.5 gm. of absolute ethanol and 34.5 g. of distilled water is prepared and used with a propellant blend of 118.0 g. of dichlorodifluoromethane and 472.0 g. of dichlorotetrafluoroethane to fill aerosol containers to a total fill weight of 17.5 g. each. The containers are equipped with pharmaceutical grade metering valves of 50 mg. delivery capacity. Each actuation thus releases 100 mcg. of MJ 9184 isethionate equivalent to 75 mcg. of MJ 9184 base.

What is claimed is:

1. A method for exerting an anorexigenic effect in a mammal having the need for reducing food consumption which comprises administering to said mammal an effective anorexigenic dose of a compound selected from the group consisting of 2'-hydroxy-5'-[1-hydroxy-2-(2-methyl-1-phenyl-2-propylamino)ethyl]-methanesulfonanilide and the pharmaceutically effective acid addition and metal salts thereof.

2. The method of claim 1 wherein said dosage amount is in the range of 2 mcg. to 1 mg. of said compound per kilogram of body weight of said mammal.

3. The method of claim 1 wherein a 2'-hydroxy-5'-[1-hydroxy-2-(2-methyl-1-phenyl-2-propylamino)ethyl]methanesulfonanilide pharmaceutically acceptable acid addition salt is employed.

4. The method of claim 1 wherein 2'hydroxy-5'-[1-hydroxy-2-(2-methyl-1-phenyl-2-propylamino)ethyl]-methanesulfonanilide is employed.

* * * * *